United States Patent [19]
Ström

[11] Patent Number: 5,937,853
[45] Date of Patent: *Aug. 17, 1999

[54] VENTILATOR FOR RESPIRATORY TREATMENT

[75] Inventor: Christer Ström, Pitea, Sweden

[73] Assignee: Siemens Elema AB, Solna, Sweden

[*] Notice: This patent issued on a continued prosecution application filed under 37 CFR 1.53(d), and is subject to the twenty year patent term provisions of 35 U.S.C. 154(a)(2).

[21] Appl. No.: 08/743,738

[22] Filed: Nov. 6, 1996

[30] Foreign Application Priority Data

Nov. 16, 1995 [SE] Sweden ................................ 9504120

[51] Int. Cl.[6] .................................................. A61M 16/00
[52] U.S. Cl. ............................... 128/204.23; 128/204.21; 128/204.18; 600/529
[58] Field of Search ...................... 128/204.23, 204.21, 128/204.24, 204.18, 204.22; 600/529, 538

[56] References Cited

U.S. PATENT DOCUMENTS

| | | | |
|---|---|---|---|
| 4,340,044 | 7/1982 | Levy et al. ......................... | 128/204.21 |
| 5,129,390 | 7/1992 | Chopin et al. ..................... | 128/204.21 |
| 5,323,772 | 6/1994 | Linden et al. ..................... | 128/204.23 |
| 5,373,842 | 12/1994 | Olsson et al. ..................... | 128/204.21 |
| 5,385,142 | 1/1995 | Brady et al. ....................... | 128/204.23 |
| 5,458,137 | 10/1995 | Axe et al. ........................... | 128/204.23 |
| 5,522,382 | 6/1996 | Sullivan et al. ................... | 128/204.23 |
| 5,540,219 | 7/1996 | Mechlenburg et al. ........... | 128/204.23 |
| 5,542,415 | 8/1996 | Brody ................................. | 128/204.23 |
| 5,546,933 | 8/1996 | Rapoport ........................... | 128/204.23 |
| 5,551,418 | 9/1996 | Estes et al. ........................ | 128/204.23 |
| 5,551,419 | 9/1996 | Froehlich .......................... | 128/204.23 |

FOREIGN PATENT DOCUMENTS

| | | | |
|---|---|---|---|
| 0 402 951 | 12/1990 | European Pat. Off. ....... | A61M 16/00 |
| 0 459 647 | 12/1991 | European Pat. Off. ....... | A61M 16/00 |
| 0 615 764 | 9/1994 | European Pat. Off. ....... | A61M 16/00 |

OTHER PUBLICATIONS

Servo Ventilator 300 Operating Manual, Chapter 5, Siemens–Elema AB, May, 1993.

*Primary Examiner*—John G. Weiss
*Assistant Examiner*—V. Srivastava
*Attorney, Agent, or Firm*—Hill & Simpson

[57] ABSTRACT

A ventilator for respirator treatment includes a gas delivery unit and a regulating unit arranged to control the gas delivery unit to deliver gas to a patient according to prescribed parameter values to obtain sufficient ventilation of the patient. Sensors are provided for sensing respiration efforts of the patient and to control the regulating unit to adapt an operation cycle of the gas delivery unit to sensed respiration efforts of the patient. The regulating unit controls the gas delivery unit also to deliver a pressure or volume support to the respiration of the patient to a predetermined resulting total pressure or volume level. If an apnea exceeding a predetermined length of time is detected by the sensor, the regulating unit controls the gas delivery unit to deliver gas to the patient according to the aforementioned prescribed parameter.

16 Claims, 2 Drawing Sheets

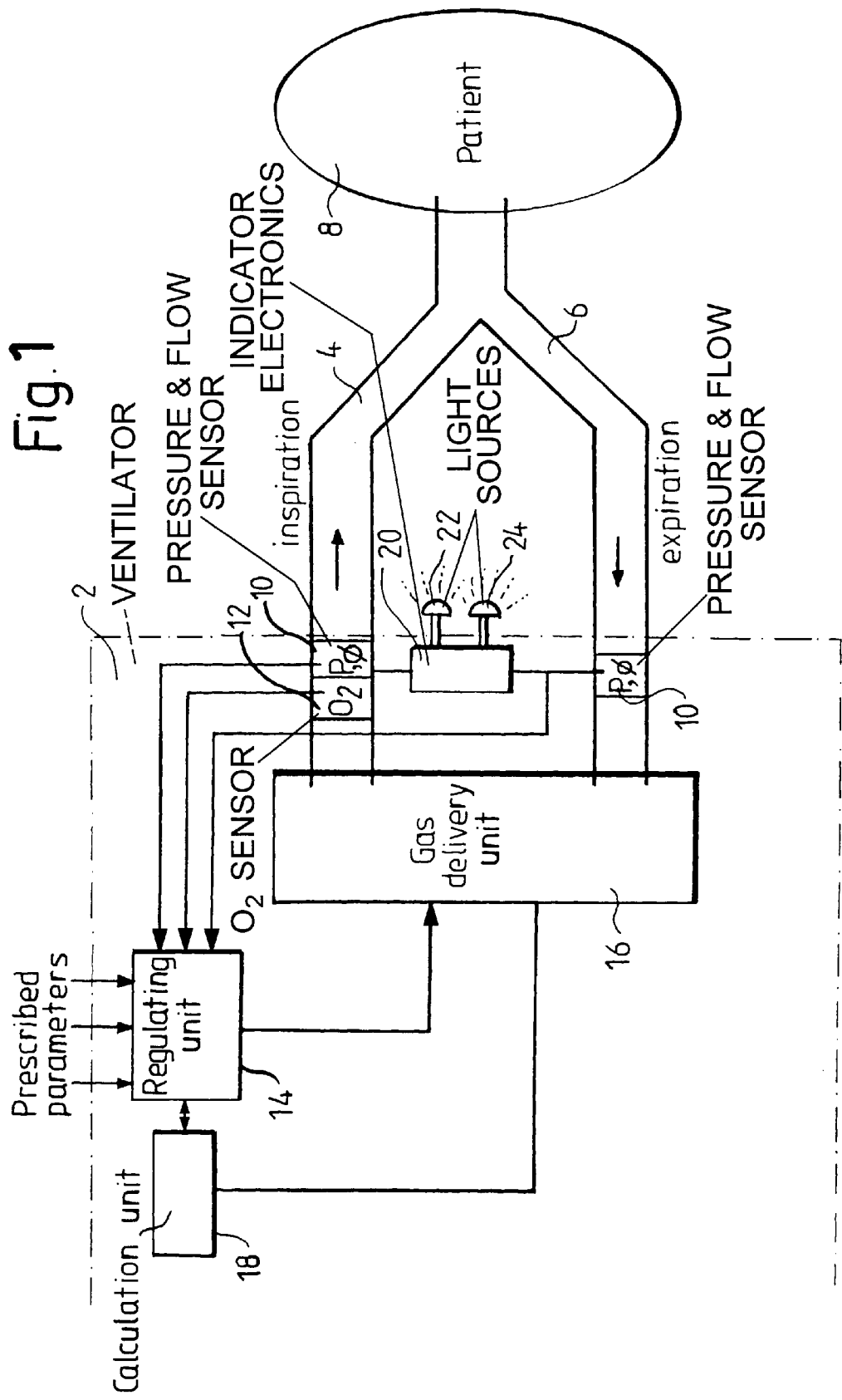

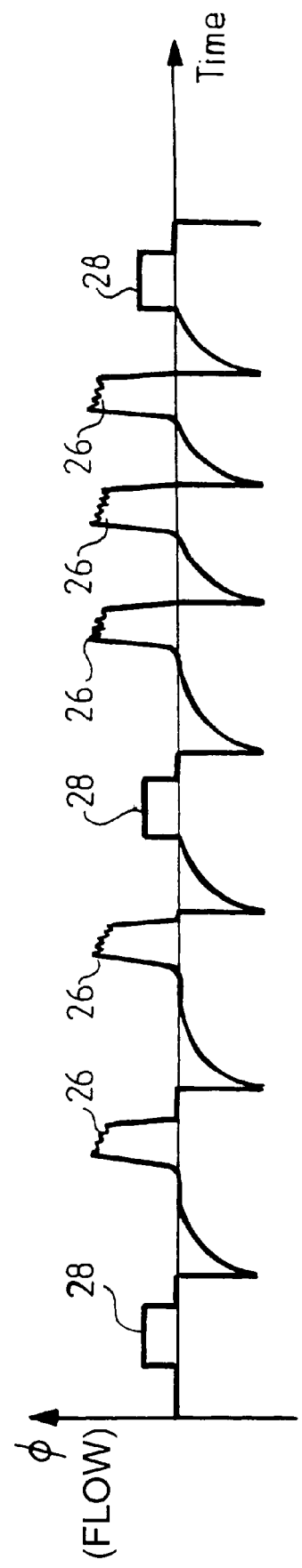

VENTILATOR FOR RESPIRATORY TREATMENT

BACKGROUND OF THE INVENTION

1. Field of the Invention

The present invention relates to a ventilator for respiratory treatment, of the type having gas delivery means, regulating means arranged to control the gas delivery means to deliver gas to a patient to obtain sufficient ventilation and sensing means for detecting an apnea of the patient, the sensing means being connected to the regulating means which are disposed to control said gas delivery means to deliver gas to the patient according to prescribed parameter values, if an apnea exceeding a predetermined length is detected.

2. Description of the Related Art

A common problem encountered in the practice of critical care medicine is that a severely ill patient will "fight" the ventilator, that is respiration efforts by the patient are non-synchronous to the operation of the ventilator. This problem can give rise to pain, hypoxia or hypoventilation of the patient. It is of utmost importance in such a situation that the ventilation pattern delivered by the ventilator and set by a clinician does not restrict the patient's own desired breathing pattern, as this might inflict damage to the lung.

If this situation occurs and the ventilator is operating in a so-called controlled ventilation mode, that is in a mode in which the ventilator is working according to preset parameter values, each respiration effort by the patient will be rewarded by the delivery of one tidal volume as set by the clinician, no more and no less, and this only under the presumption that the triggering level of the ventilator has been set judiciously so the patient can trigger a ventilator delivered tidal breath. To cope with this situation, common practice is to sedate the patient and administer a neuromuscular blocking drug, which will induce muscle paralysis and stop further respiration attempts by the patient. The use of neuromuscular blocking drugs in intensive care has, however, been frequently criticized, because of lack of knowledge about the effects of longterm usage.

Another way of handling the problems in connection with non-synchronism between the operation of the ventilator and the respiration efforts of the patient is to manually change the breathing mode of the ventilator, so the respiration of the patient is supported by the ventilator, thereby allowing the patient to breath spontaneously and receive proper pressure or volume support. This operating mode of the ventilator will give the patient the possibility to breath at his own leisure and give the clinician time to analyze the state and then take proper measures to treat underlying problem in a way other than by using neuromuscular blocking drugs as mentioned above.

The situation of a patient fighting a ventilator, however, can be quite alarming and very often no time is available for analysis, so there is a tendency to treat the patient according to a routine prescription and leave the analysis until the chronic situation is abated. This can prolong the time the patient stays connected to the ventilator, increase the complication rate and deteriorate the clinical outcome.

The above-mentioned modes of operation of a ventilator for respiratory treatment are described in the publication Servo Ventilator 300, Operating Manual, chapter 5, issued by Siemens-Elema AB, May 1993.

Even if the patient is not fighting the ventilator as described above, there is a risk that the patient will spend too long a time connected to the ventilator by using machine controlled ventilation for extended periods of time. This can result in weakening and even wasting of the respiratory muscles of the patient and prolonged time for weaning the patient off the ventilator. Therefore, this situation also presents a risk of increased complication rate and impaired clinical outcome.

The disadvantages of the current ventilator technique thus reside in the fact that the breathing mode determined by the ventilator forms an obstacle to attempts of spontaneous respiration by the patient, and this situation can only be altered by manually changing the settings controlling the operation of the ventilator.

SUMMARY OF THE INVENTION

An object of the present invention is to remedy the above disadvantages of prior art ventilators and to provide a ventilator for automatically choosing and adapting the ventilation mode to the needs of the patient.

The above object is achieved in accordance with the principles of the present invention in a ventilator for respiratory treatment having a gas delivery unit, a regulating unit which controls the gas delivery unit so as to deliver gas to a patient to ventilate the patient, and a sensing unit for detecting an apnea of the patient, the sensing unit being connected to the regulating unit so as to permit control of the gas delivery unit by the regulating unit for delivering gas to the patient according to prescribed parameter values if an apnea exceeding a predetermined length is detected. The sensing unit senses respiration efforts of the patient and supplies a signal to the regulating unit to cause the regulating unit to adapt an operation cycle of the gas delivery unit to the sensed respiration efforts of the patient, and then to cause the gas delivery unit to deliver an auxiliary support which makes up any deficiency from a predetermined total value of a particular respiration parameter.

The auxiliary support may be in the form of additional volume if the predetermined total parameter in question is a volume level, or can be a delivery of additional pressure, if the predetermined total parameter is a pressure level.

In the inventive ventilator for respiratory treatment of patients, the ventilator automatically adapts its mode of operation to give the patient a proper support, in a range from a situation with a patient without any respiratory drive at all to a patient having a practically sufficient spontaneous respiration, and each intermediate degree of defective respiration.

Thus the ventilator according to the invention is automatically switched, in response to respiratory efforts of the patient, to an operation mode in which the spontaneous respiration of the patient is supported to obtain sufficient ventilation. In the case of an apnea exceeding a predetermined length of time, the ventilator is switched to operate according to prescribed parameter values so as to also in this situation obtain sufficient ventilation of the patient. Thus, every apnea will also be backed up, making the ventilator safe in this respect.

Each prescribed parameter value has one or more parameter-producing factors associated therewith which can be increased, if necessary, to bring the parameter value to its prescribed parameter value. Pressure and volume, respectively, are the most common of these parameter-producing factors, because almost every ventilation parameter value of interest can be adjusted (changed) by changing the volume or pressure of the respiratory gas delivered to the patient. Therefore, if the parameter value in question falls below a prescribed parameter value, pressure or volume can be increased, as needed, to make up the deficiency if an apnea exceeding a predetermined length is detected.

In an embodiment of the ventilator of the invention, the regulating means increase the tidal volume to maintain the set minute volume, if the sensed respiration rate decreases below a value corresponding to said prescribed operation cycle. The tidal volume can be increased to a maximum of 50% above the tidal volume value corresponding to the set minute volume and operation cycle. Thus, if the patient's spontaneous breathing rate drops below the prescribed value, the tidal volume will increase in order to maintain the prescribed minute volume.

According to another embodiment of the ventilator of the invention, the regulating means control calculation means provided to calculate the impedance of the airway of the patient in response to a sensed spontaneous respiration effort of the patient. Additionally regulating means control the gas delivery means in response to the calculated impedance to give proper volume support in order to deliver a tidal volume to the patient corresponding to the set minute volume and operating cycle. This is important if the patient makes spontaneous breathing efforts during the initiation of the ventilation treatment, and after three or four breaths the ventilator will in this way deliver a proper support level to the patient.

Thus, in the so-called support mode the patient controls the breathing rate and gets support from the ventilator on every initiated breath.

According to another embodiment of the ventilator of the invention the regulating means, reset the calculation means for a new attempt of impedance calculation n case of an impedance calculation failure and, in case of repeated impedance calculation failures such as after a predetermined number of such failures, the regulating means control the gas delivery means to deliver respiration support to the patient according to the prescribed parameter values for a certain time, whereupon the regulating means control the calculation means to make a new attempt at impedance calculation and the procedure above is repeated. This is an important advantage, since in certain circumstances it can be difficult because of instable conditions to calculate a proper airway impedance for the ventilator. This might lead to a situation where the ventilator will repeatedly reset in order to find a proper starting point. This is avoided with this embodiment of the ventilator since after a predetermined number of unsuccessful calculation attempts the ventilator switch to so-called controlled ventilation, respiration gas is delivered to the patient according to prescribed parameter values for a certain time, whereupon new attempts are made to calculate the impedance. This procedure can be repeated several times.

In another embodiment of the ventilator of the invention, the regulating means control the gas delivery means to deliver respiration support to the patient according to prescribed parameter values corresponding to single breaths synchronized to sensed respiration efforts of the patient at intervals equal to a number of complete respiration periods. According to this embodiment the ventilator is operated at a certain base rate also when the patient is spontaneously breathing to give an extra respiration support, the supporting gas pulses delivered by the ventilator being synchronized to the spontaneous respiration of the patient.

In another embodiment, indicator means are provided to indicate very sensed breath to inform the clinician about the current mode of operation of the ventilator.

In a further embodiment the sensing means are a flow sensor, which makes reliable triggering of the ventilator by respiration efforts of the patient possible.

BRIEF DESCRIPTION OF THE DRAWINGS

FIG. 1 schematically shows a block diagram of an embodiment of the ventilator according to the invention, an example.

FIG. 2 is a flow diagram for a special form of ventilator support of spontaneous respiration of a patient using the ventilator of FIG. 1.

DESCRIPTION OF THE PREFERRED EMBODIMENTS

In FIG. 1 a ventilator 2 is connected through an inspiration tube 4 and an expiration tube 6 to a patient 8. Sensors 10, such as pressure or flow sensors, are provided in the inspiration tube 4 and in the expiration tube 6. In the inspiration tube 4 an oxygen sensor 12 is situated as well, to monitor the oxygen content of the breath delivered to the patient.

The sensors 10 are connected to a regulating unit 14 which in turn is connected to a gas delivery unit 16 for controlling the delivery of gas to the patient 8 in response to signals from the sensors 10 and/or in response to externally prescribed parameter values as described below. The sensors 10 thus serve as means for triggering a mode of operation of the ventilator suitable for the condition of the patient, and the sensors 10 can operate as a flow triggering or pressure triggering means for the ventilator.

The regulating unit 14 is also connected to a calculation unit 18 which is connected to the gas delivery unit 16 as well. The calculation unit 18 is provided for calculation of the impedance of the airway of the patient 8 as will also be described in greater detail below.

An indicator arrangement including electronics 20 and light sources, e.g. in the form of light emitting diodes 22 and 24, is also connected to the sensors 10 for indicating spontaneous respiration of the patient 8 to the operator of the ventilator.

Those parts of the ventilator 2 which are not of importance for the explanation of the invention have been omitted from FIG. 1.

The operation of the ventilator 2 will now be described in greater detail by three coupled operation modes.

1. Pressure Controlled Ventilation—Pressure Supported Ventilation

The ventilator 2 operates according to parameters prescribed by the operator. These parameters set by the operator are the pressure above the Post End Expiratory Pressure (PEEP), the operation cycle and oxygen content of breath to be delivered. With the exception of the operation cycle the same parameters are set also for the pressure supported ventilation.

In the case of pressure controlled ventilation the ventilator 2 will consequently operate according to these prescribed parameters up to the point where the patient triggers the ventilator 2 to change its mode of operation to pressure supported ventilation. Thus, if the patient starts his own breath, detected by the sensors 10, the ventilator 2 will respond by giving a pressure support to the patient up to the pressure level set by the operator and the breathing rate will be controlled by the sensed respiration efforts of the patient. Every breath initiated by the patient will be supported from the ventilator 2, i.e. a respiration effort sensed by the sensors 10 triggers the regulating unit 14 to control the gas delivery unit 16 to give a pressure support to the patient for each detected breath.

If the patient becomes apneic for a certain period of time, e.g. 15–18 seconds, that is not spontaneous respiration is sensed by the sensors 10 during this time, the ventilator 2 is switched to the controlled mode of operation. In this mode the regulating unit 14 controls the gas delivery unit 16 to give a pressure controlled ventilation to the patient according to the prescribed parameters, until the ventilator 2 is once again triggered to the pressure support ventilation mode by respiration efforts by the patient.

If the patient 8 should make spontaneous breathing efforts during the initiation of the ventilator treatment, these breathing efforts will be detected by the sensors 10 and in response thereto the regulating unit 14 will command the gas delivery unit 16 to deliver pressure supported breaths according to the set values.

The components 20, 22 and 24 of the indicator arrangement are connected to the sensors 10 to indicate to the operator whether the ventilator 2 is operating in the controlled or the supported mode. Thus, the indicator arrangement is triggered by every breath such that a light emitting diode 22 is illuminated in response to every sensed breath.

2. Volume Controlled Ventilation—Volume Supported Ventilation

In the volume controlled mode of ventilation the prescribed parameters delivered to the regulating means 14 are minute volume, PEEP, operation cycle and oxygen content of the breath to be delivered. With the exception of the operation cycle these parameters also determine the volume supported ventilation.

In the volume controlled mode of ventilation the ventilators controlled to operate with the above mentioned prescribed parameters up to the point where a respiration effort is sensed by a sensors 10 which triggers the ventilator 2 to change its mode of operation. In this support mode the ventilator 2 will respond to a patient triggered breath by giving a volume supported breath with the pressure level of the first supported breath corresponding to the pause pressure of the volume controlled breath. As the resulting flow is detected in the inspiration tube 4 the regulating means 14 will adjust the support level of the gas delivery means in order to maintain the set tidal volume. Thus, the patient controls the breathing frequency and is supported from the ventilator on every initiated breath.

If the sensed spontaneous breathing frequency of the patient drops below a value corresponding to the prescribed operation cycle for the controlled ventilation mode, the regulating unit 14 will control the gas delivery unit 16 to increase the tidal volume to maintain the prescribed minute volume. The tidal volume can be increased up to a maximum of 50% above the tidal volume value corresponding to the prescribed minute volume and operation cycle.

If the patient should make spontaneous breathing efforts during the initiation of the ventilator treatment which are detected by the sensors 10, the regulating unit 14 will control the calculation unit 18 to calculate the impedance of the airway such that the proper support level can be delivered for obtaining the set tidal volume. The impedance is determined by applying, with the aid of the gas delivery unit 16, a certain pressure, e.g. 5 cm $H_2O$, and the resulting gas flow is measured with the flow meter in the inspiration tube 4. From this value the impedance can be calculated and the regulating unit 14 can control the gas delivery unit 16 to give the proper support level in order to get the set tidal volume. This proper level is reached after three or four breaths.

The operation frequency or operation cycle of the ventilator 2 is adjusted to the patient's spontaneous respiration rate in the same way as described above under point 1, and if an apnea lasting for a period of 15–18 seconds is detected by the sensors 10 the ventilator 2 will be switched to the volume controlled ventilation mode until the sensors 10 once again detect a respiration effort from the patient which triggers the regulating unit 14 to control the gas delivery unit 16 according to the volume supported mode of operation. Also in this embodiment the LED 22 will be illuminated on every sensed breath from the patient 8, thus informing the operator about the current mode of operation of the ventilator 2.

3. Pressure Regulated Volume Controlled Ventilation—Volume Supported Ventilation—Volume Controlled Ventilation In the pressure regulated volume controlled (PRVC) mode of ventilation the prescribed parameters are the same as for the volume controlled mode of ventilation described under point 2 above and similarly, with the exception of the operation cycle, the same parameters also apply to the volume supported mode of ventilation.

When the RPVC mode of ventilation is started the ventilator 2 will operate according to the prescribed parameters up to the point where the ventilator 2 is triggered to change its mode of operation by respiration efforts sensed by the sensors 10.

If the regulating unit 14 is triggered by sensed respiration efforts of the patient to change the mode of operation, the gas delivery unit 16 will be controlled to respond by giving a volume supported breath with the pressure level of the first supported breath corresponding to the level of the PRVC breath. The resulting flow in the inspiration tube 4 will be measured and the regulating unit 14 will adjust the support level of the gas delivery unit 16 in order to maintain the set tidal volume corresponding to the prescribed minute volume and operation cycle. The patient 8 will then control the breathing frequency and get support from the ventilator 2 on every initiated breath, and if the spontaneous breathing rate of the patient 8 drops below the prescribed value for the controlled mode of ventilation, the tidal volume will be increased as described in relation to the embodiment under point 2 above.

Also as described above under point 2, the impedance of the airway is calculated by the calculating unit 18 if the patient should make spontaneous breathing efforts during the initiation of the ventilator treatment, so as to be able to deliver the proper support level for maintaining the tidal volume equal to the set value.

If an apnea is detected for a period of 15–18 seconds the ventilator 2 will switch back to the controlled mode in the same way as described for the previous embodiments under points 1 and 2.

Under certain circumstances of instability it can be difficult to calculate a proper airway impedance for the ventilator 2 on initiating PRVC. This might lead to a situation where the ventilator 2 will repeatedly be rest in order to find a proper starting point. To avoid this situation the regulating unit 14 changes mode of operation, after, for example, three unsuccessful attempts, to the volume controlled mode of ventilation. This situation is suitably indicated to the operator by a blinking volume control LED 22 and a continuously illuminated PRVC LED 24.

After a period of 2–5 minutes the regulating unit 14 is controlled to agin attempt to change mode of operation to the PRVC mode of ventilation and if the attempt is successful, the usual start-up sequence is executed. A subsequent switching from the PRVC mode of ventilation to the volume supported mode may be performed as described above. If initiation once again fails, the volume controlled mode of respiration is resumed and a new attempt is made after another 2–5 minutes.

The start-up of the PRVC mode of ventilation can also be initiated manually by turning a RESET-button.

Also in this embodiment suitable indicator means are provided to inform the operator about the current mode of operation of the ventilator.

The regulating unit 14 can also control the gas delivery unit 16 to deliver a special kind of respiration support to a patient 8 having a certain spontaneous respiration, as shown in FIG. 2 which shows gas flow Φ as a function of time illustrating this situation. The pulses 26 are produced by spontaneous respiration of the patient and this respiration is supported by pulses 28 delivered with a predetermined base rate. The volume of these supporting pulses 28 corresponds to the volume of a single breath and these supporting pulses 28 are synchronized to the sensed respiration efforts of the patients, and are delivered at intervals equal to a complete number of respiration periods.

Although the invention has been described with respect to preferred embodiments, it is not to be so limited as changes and modifications can be made therein which are within the full intended scope of the invention as defined by the appended claims.

I claim as our invention:

1. A ventilator for respiratory treatment of a respirating subject comprising:

gas delivery means for delivering respiratory gas to a subject;

regulation means for controlling said gas delivery means to deliver respiratory gas according to a mode of operation, for a non-spontaneously respirating subject, selected from the group consisting of a control mode, wherein said regulating means operates said gas delivery means to impose a breathing pattern according to prescribed control mode parameters, and a support mode, wherein said regulating means operates said gas delivery means to assist spontaneous breathing by said subject using support mode parameters;

sensing means for sensing a beginning of spontaneous respiration efforts of said subject and for emitting a signal to said regulating means in response to a sensed beginning of spontaneous respiration effort; and said regulating means being connected to said sensing means and comprising means for changing the mode of operation of the ventilator, for when the ventilator is operating in said control mode, automatically switching control of the gas delivery means to deliver gas in said support mode, in response to said signal from said sensing means.

2. A ventilator as claimed in claim 1 wherein said means for adapting the mode of operation comprise means for automatically switching control of the gas delivery means back to said control mode upon an absence of sensed respiration efforts by the sensing means for a predetermined time period.

3. A ventilator as claimed in claim 1 wherein the control mode comprises a pressure control wherein said prescribed control mode parameters comprise pressure above PEEP, operation cycle and oxygen content of a breath to be delivered, and wherein said support mode comprises pressure support.

4. A ventilator as claimed in claim 1 wherein the control mode comprises volume control and wherein said prescribed parameters comprises tidal volume, operation cycle and oxygen content of a breath to be delivered, and wherein said support mode comprises volume support wherein a prescribed support mode parameter comprises minute volume.

5. A ventilator as claimed in claim 4 wherein said regulating means comprises means for controlling the gas delivery means for increasing the tidal volume to maintain the prescribed minute volume, if a rate of respiration efforts sensed by the sensing means decreases below a prescribed value.

6. A ventilator as claimed in claim 5 wherein the regulating means comprise means for limiting an increase of the tidal volume by said gas delivery means to a maximum of 50% above the prescribed tidal volume.

7. A ventilator as claimed in claim 4 wherein the support mode comprises volume support and wherein the regulating means comprise means for controlling the gas delivery means for delivering gas according to the volume support mode, for a first respiration effort sensed by the sensing means, with a pressure level corresponding to a pause pressure of the volume control mode and for controlling the gas delivery means for adjusting delivery of gas in the volume support mode for subsequent breaths to maintain the tidal volume equal to a value corresponding to the prescribed minute volume and operation cycle.

8. A ventilator as claimed in claim 1 wherein the control mode comprises pressure regulated volume control, and wherein said prescribed control mode parameters comprise tidal volume, operation cycle and oxygen content of a breath to be delivered, and wherein the support mode comprises volume support wherein a prescribed support mode parameter comprises minute volume.

9. A ventilator as claimed in claim 8 wherein said regulating means comprise means for controlling the gas delivery means for increasing the tidal volume to maintain the prescribed minute volume, if a rate of respiration efforts sensed by the sensing means decreases below a prescribed value.

10. A ventilator as claimed in claim 9 wherein the regulating means comprise means for limiting increase of the tidal volume by said gas delivery means to a maximum of 50% above the prescribed tidal volume.

11. A ventilator as claimed in claim 8 wherein the regulating means comprises means for emitting an enabling signal in response to a spontaneous respiration effort of the patient sensed by the sensing means, and wherein said ventilator comprises calculating means, enabled by said enabling signal, for calculating an impedance of an airway of said subject, and wherein the regulating means comprise means for controlling the gas delivery means dependent on the impedance calculated by the calculation means to produce volume support for delivering a tidal volume to the subject corresponding to the prescribed minute volume and operation cycle.

12. A ventilator as claimed in claim 1 wherein the regulating means comprise means for resetting the calculation means, if the calculation means fails to calculate the impedance for a new attempt at impedance calculation, if the calculation means repeatedly fails to calculate impedance for a predetermined number of times, for controlling the gas delivery means to deliver gas according to the volume control mode for a predetermined time. And for thereafter controlling the calculation means to again attempt impedance calculation.

13. A ventilator as claimed in claim 1 wherein the regulating means comprise means for controlling the gas delivery means for delivering gas control mode having a prescribed control mode parameter comprising single breaths synchronized to respiration efforts sensed by the sensing means at intervals equal to a predetermined number of respiration periods.

14. A ventilator as claimed in claim 1 wherein said sensing means comprise a flow meter.

15. A ventilator as claimed in claim 1 wherein said control mode comprises a mode selected from the group consisting of pressure control, volume control and pressure regulated volume control.

16. A ventilator as claimed in claim 1 wherein said support mode comprises a mode selected from the group consisting of pressure support and volume support.

* * * * *